United States Patent [19]

Childs

[11] 4,402,212

[45] Sep. 6, 1983

[54] OCTANE NUMBER MEASURING SYSTEM

[75] Inventor: W. Ves Childs, Bartlesville, Okla.

[73] Assignee: Phillips Petroleum Company, Bartlesville, Okla.

[21] Appl. No.: 271,157

[22] Filed: Jun. 8, 1981

[51] Int. Cl.³ .................... G01L 23/22; G01N 33/22
[52] U.S. Cl. .................................................. 73/35
[58] Field of Search ............................. 73/35, 863.73

[56] References Cited

U.S. PATENT DOCUMENTS

| | | | |
|---|---|---|---|
| 2,936,609 | 5/1960 | Pope, Jr. et al. | 73/35 |
| 3,071,005 | 1/1963 | Skidmore | 73/863.73 |
| 3,183,708 | 5/1965 | Roddick | 73/35 |
| 3,318,136 | 5/1967 | Payne et al. | 73/35 |
| 3,469,954 | 9/1969 | Hoffman | 73/35 X |
| 3,503,722 | 8/1970 | Weber et al. | 73/35 X |
| 3,933,165 | 1/1976 | Budzak et al. | 73/863.73 |
| 3,969,922 | 7/1976 | Baker et al. | 73/35 |
| 4,010,358 | 3/1977 | Morris | 73/35 X |
| 4,036,063 | 7/1977 | Roof et al. | 73/864.83 X |

OTHER PUBLICATIONS

"Mercedes-Benz 280E", Cam and Driver Magazine pp. 62-68, Mar. 1977.

*Primary Examiner*—James J. Gill

[57] ABSTRACT

First and second reference fuels having different known octane numbers and a test fuel having an unknown octane number are each provided individually to the fuel inlet of an engine at a desired flow rate. The sample valve is utilized to inject test fuel into a fuel flowing to the fuel inlet of the engine so as to be able to determine the octane number of a test fuel based on only a small sample.

9 Claims, 3 Drawing Figures

OCTANE NUMBER MEASURING SYSTEM

This invention relates to method and apparatus for determining the octane number of a fuel. In one aspect this invention relates to method and apparatus for determining the octane number of the fuel when only a small sample of the fuel is available or when it is desired to use only a small sample of fuel for test purposes.

There are many standard methods for determining the octane number of various fuels. Examples of these standard methods include ASTM Method D-2699-79 for the research octane number of gasoline and ASTM Method D-2700-79 for the motor octane number of gasoline. To determine the octane number of a test fuel in accordance with the ASTM methods, an ASTM-CFR engine is operated with the test fuel and with at least two reference fuels under conditions that will cause maximum knock. A pressure transducer is utilized to monitor the cylinder pressure and produce a voltage signal that is proportional to the rate of change in that pressure. A detonation meter is utilized to filter, integrate and amplify the output of the pressure transducer to produce a voltage signal that is proportional to the knock intensity. This signal is utilized to drive a knock meter which gives a scale reading relating to knock intensity. A comparison of the knock meter readings produced by the combustion of the reference fuels with the knock meter reading produced by the combustion of the test fuel is utilized to estimate the octane number of the test fuel.

The ASTM methods and most other standard methods require that the engine must be operated under maximum knocking conditions for each fuel being provided to the engine. In the ASTM method, the air/fuel ratio that results in maximum knock is found by a successive approximations method. The fuel level in a carburetor float bowl is moved up and down while the knock meter response is noted. This takes considerable fuel.

In the case of test fuels produced in a laboratory, many times there is only a very small quantity of the test fuel available for determining the octane number. Also, in commercial operations where continuous monitoring of the fuel being produced is required, it may be desirable to use small samples to determine the octane number to avoid wasting fuel. It is thus desirable to be able to measure the octane number of a test fuel with a small amount of the test fuel and it is an object of this invention to provide method and apparatus for reducing the quantity of fuel required to determine the octane number of a test fuel.

In accordance with the present invention, a sample valve is utilized to introduce small samples of a test fuel into the fuel flowing to the test engine. One of the reference fuels being utilized to determine the octane number of the test fuel may be utilized as the carrier fluid. Use of the separate valve provides a means by which various small samples in the test fuel may be handled easily and also provides a means by which an accurate determination of when the small sample of test fuel enters the test engine can be made because the actuation time of the sample valve will be known.

Other objects and advantages of the invention will be apparent from the foregoing brief description of the invention and from the claims as well as from the detailed description of the drawings in which:

The invention is described in terms of a preferred embodiment in which a pump is utilized to supply fuel to the test engine. Also, density measurements are utilized as will be more fully described hereinafter to determine the flow rate at which the fuel should be supplied to the test engine. This invention however is applicable to other techniques for supplying a fuel to an engine and may be utilized without the density measurement. The density measurement might not be required in the case of a process in which the octane number of a fuel being produced is continuously monitored. The flow rate of fuel to the test engine may be maintained constant with periodic injections of the test fuel into the reference fuel or other carrier fluid flowing to the test engine. This could be utilized to provide indications that the octane number of the fuel being produced has changed over a period of time.

The invention is also described in terms of a particular sample valve configuration. Any suitable valve system could be utilized so long as a small sample of test fuel can be injected into a fuel stream flowing into a test engine.

Figure 1:
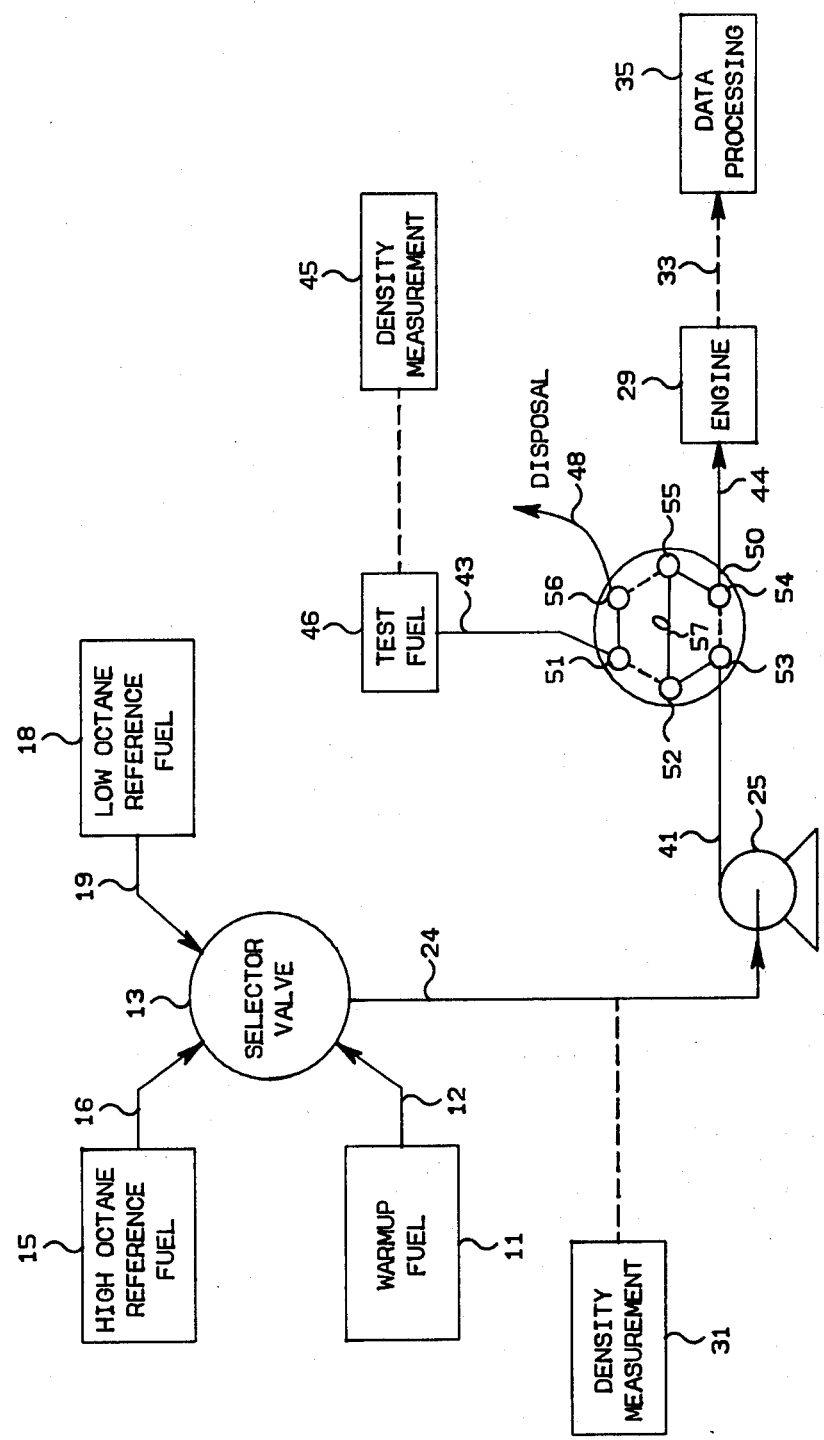
FIG. 1 is a simplified diagrammatic illustration of apparatus for determining the octane number of a fuel in accordance with the present invention.

Referring now to the drawings and in particular to FIG. 1, a warm-up fuel is provided from the supply 11 through conduit means 12 to the selector valve 13; a high octane reference fuel is provided from the supply 15 through conduit means 16 to the selector valve 13; and a low octane reference fuel is provided from the supply 18 through conduit means 19 to the selector valve 13. The supplies for the various fuels may be under pressure if desired or gravity flow may be utilized. A particular fuel is selected through use of the selector valve 13 and is provided through conduit means 24 to the pump 25. The fuel flowing through conduit means 24 is provided from the pump 25 through conduit means 41 to the port 53 of the sample valve 50.

Any suitable sample valve may be utilized to supply the test fuel to the test engine. Preferably, the sample valve 50 is a six port sample valve referred to as a Model X manufactured by Applied Automation, Inc. The sample valve 50 is a two positioned sample valve. Fluid flow is as illustrated by the dotted lines between the ports when the sample valve 50 is in a first position. Fluid flow is as illustrated by the solid lines when the sample valve 50 is in a second position. With the sample valve 50 in the first position, the fuel flowing through conduit means 41 is provided from port 53 to port 54 and thus to the engine 29 through conduit means 44.

A test fuel is provided from supply 46 through conduit means 43 to the port 51 of the sample valve 50. The fuel supply 46 may be under pressure or a pump may be used to supply test fuel to the port 51. With the sample valve 50 in the first position, the fuel flowing through conduit means 43 is provided from port 51 to port 52 and thus through the sample loop 57 to port 55. The fuel is then provided to port 56 and then through conduit means 48 to a disposal. It is noted that the fuel flowing through conduit means 48 may be supplied to a container for reintroduction into the test fuel supply 46.

With the sample loop 57 filled with a test fuel, the sample valve 50 will be switched to the second position at a desired time. The flow of test fuel through conduit means 43 is provided from port 51 to port 56. The fuel flowing through conduit means 41 is provided from port 53 to port 52 and thus through the sample loop 57 to port 55. From port 55 the fuel is provided to port 54 and thus through conduit means 44 to the engine 29. The test fuel contained in the sample loop 57 will be provided as a more or less discrete plug for delivery to the engine 29.

The pumping rate of the pump 25 is manipulated in such a manner that the particular fuel flowing through conduit means 44 flows at the mass flow rate which results in maximum knock. Prior to introduction of the test fuel into the fuel flowing to the engine 29, the pumping rate of the pump 25 is manipulated in such a manner that the fuel flowing through conduit means 44 flows at the mass flow rate which will result in maximum knock if the test fuel were flowing to the engine 29. Thes, when the test fuel is introduced into the fuel flowing to the engine 29, the flow rate will be such as to provide maximum knock during the interval in which the slug of test fuel is combusted in the engine 29.

It is noted that, for a wide range of hydrocarbon base fuels such as aromatics, alkylates and catalytic cracker gasolines, the mass flow rate of the fuel which gives maximum knock is substantially constant for a particular engine operating at a particular speed. For example, the research octane number is determined in accordance with ASTM method D-2699-79 by operating a standard ASTM-CFR engine at 600 RPM. Under these conditions the mass flow rate of each fuel which results in maximum knock is about 13 grams per minute. The required mass flow rate will vary with engine type and engine speed but once the mass flow rate that results in maximum knock for a particular engine operating at a particular speed is determined, this mass flow rate can be used for both the test fuel and the reference fuel.

Typically, the volume flow rate of whatever fuel is flowing through conduit means 44 will be known. Any suitable method may be utilized to determine the actual mass flow rate based on the known volume flow rate. Preferably, the density measurement of whatever fuel is flowing through conduit means 24 by the density measuring device 31 or the density measuring device 45 is utilized to determine the actual mass flow rate. A suitable density measuring device is a Metler-Parr Density measuring device manufactured by Metler. The density of the fuel is multiplied by the volume flow rate to give the actual mass flow rate. Other techniques such as weighing a known volume of the fuel and multiplying the weight of the known volume of fuel by the volume flow rate can be utilized. Whatever technique is used, the flow rate of the fuel flowing through conduit means 44 can be set directly to the mass flow rate which results in maximum knock by adjusting the volume flow rate until the desired mass flow rate is achieved. The successive approximation technique required by the ASTM methods is not required to find the flow rate of the fuel which will result in maximum knock.

A pressure transducer associated with the engine 29 monitors the cylinder pressure in the engine 29 and produces a voltage signal 23 which is proportional to the rate of change of the cylinder pressure. Signal 33 is processed by the data processing equipment 35 to derive the knock intensity for the particular fuel being provided to the engine 29. Since the octane number of the high octane reference fuel and low octane reference fuel are known, and it is known that the engine is operating at conditions which give maximum knock for each of the fuels which are provided to the engine 29, the octane number of the test fuel can be derived directly by comparing the knock intensity of the test fuel to the knock intensity of the high octane reference fuel and the low octane reference fuel. Signal 33 may be processed by the standard ASTM methods which utilize a detonation meter and a knock meter or may be processed by other data processing techniques which may involve a computer as will be described hereinafter in conjunction with the description of FIG. 3.

In operation, the warm-up fuel flowing from the supply 11 is utilized to warm up the engine 29 and may be utilized for any calibrations required. One of the reference fuels can be used for warm up purposes if desired. After the engine has been warmed up, the high octane reference fuel, low octane reference fuel and test fuel are then provided sequentially to the engine 29. The high octane reference fuel, low octane reference fuel and test fuel may be provided to the engine 29 in any order but preferably the high octane reference fuel is provided to the engine 29, then the low octane reference fuel and then the test fuel. The warm-up fuel, high octane reference fuel or low octane reference fuel may be used as a carrier fluid to provide the sample of test fuel to the engine 29.

When it is desired to provide the test fuel to the engine 29, the pump 25 is first set to the flow rate which will provide maximum knock when the test fuel is flowing to the engine 29 based on the density measurement of the test fuel. The sample valve 50 is then switched such that the test fuel in the sample loop 57 of the sample valve 50 is provided to the engine 29 through conduit means 44. Again, the fuel flowing through conduit means 41 acts as a carrier fluid and essentially a slug of test fuel is injected into the engine 29 with the carrier fluid preceding and following the slug. The knock intensity when the test fuel is flowing to the engine 29 is determined and the octane number of the test fuel is derived as has been previously described.

For most purposes, a four octane number spread between the reference fuels as desired. The two most generally used sets of reference fuels are 90/94 and 96/100. The 90/94 pair of reference fuels is preferably used to rate test fuels in the range of about 88 to about 95 octane and the 96/100 pair of reference fuels is preferably used to rate test fuels in the range of about 95 to about 100 octane. Preferably, the high octane reference fuel and the low octane reference fuel should conform to the fuel requirements of ASTM method D-2699-79 and D-2700-79 as outlined in sections 1, 3, 5, 6. and 8, and annexes 1-7 if the research octane number or motor number of a gasolne is being determined.

Any suitable apparatus for providing the different fuels sequentially to the pump 25 can be utilized. The use of the selector valve 13 is presently preferred but individual cutoff valves could be utilized with each of the fuel supplies being concerned directly to the pump 25 if desired or a sample valve having more than 6 ports could be used. A suitable selector valve 13 is a Whitney Selector valve, Model B-43ZF52.

Any suitable pump may be utilized to provide the fuel flow to the engine 29. A suitable fuel pump 25 is a FMI Lap Pump Model RP-P-SSY-O. Since the FMI pump provides volumetric flow rate, it is necessary to convert the volumetric flow rate to a mass flow rate. As has been previously stated, this is preferably done utilizing a density measurement of the various fuels flowing through the pump 25 but can be accomplished by utilizing any suitable apparatus which results in the fuels flowing to the engine 29 at the same substantially constant mass flow rate.

Any suitable engine may be utilized for the octane number determination. The engine 29 is preferably the ASTM-CFR engine which is required in the standard ASTM method for determining octane number. The ASTM-CFR engine is a one cylinder, four cycle engine which conforms to the requirements of ASTM standard D-2699-79 and also includes a D-1 pressure transducer. Other engines may be required by other standard tests.

Figure 2:
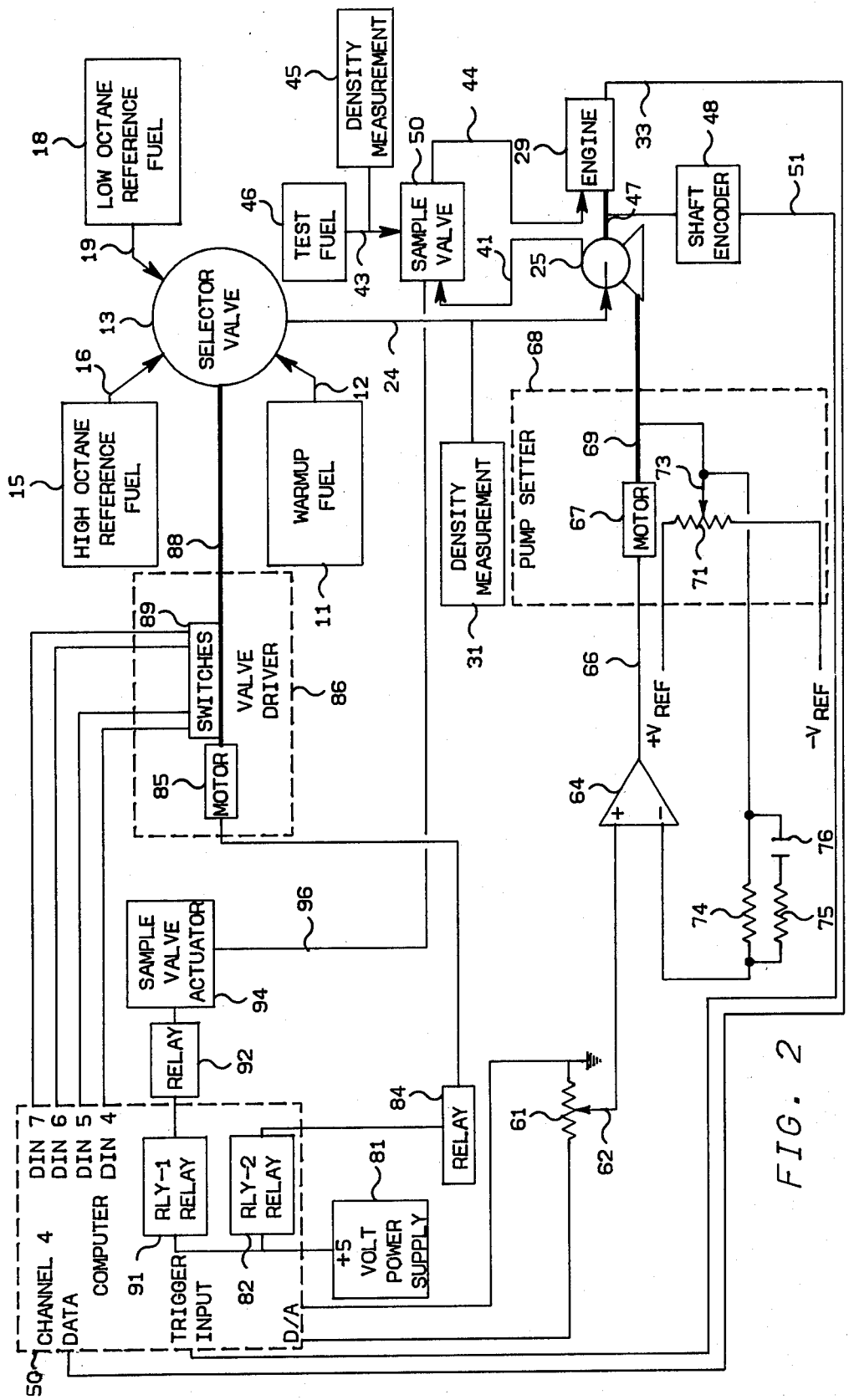
FIG. 2 is a diagrammatic illustration of the preferred computer controlled apparatus configuration for determining the octane number of a fuel in accordance with the present invention.

A preferred embodiment of the present invention in which the octane measuring system illustrated in FIG. 1 is under computer control is illustrated in FIG. 2. Referring now to FIG. 2, the octane measuring system is operated as in FIG. 1 except for the use of the computer to control the selector valve 13, the pump 25 and the sample valve 50. The engine 29 is preferably an ASTM-CFR engine as has been previously stated. The pump 25 is driven by a half-speed shaft 47 of the engine 29. A suitable shaft encoder 48 is a Disc Rotaswitch Shaft Encoder, Model X-701-360-T-C-TTL-SS manufactured by Disc Instruments. The shaft encoder 48 is operably connected to the half-speed shaft 47. The shaft encoder provides an output signal 51 which is a single transistor-transistor logic (TTL) level pulse which is delivered once per engine cycle. Signal 51 is provided to the trigger input of the computer 50 and is utilized to provide timing information to the computer 50 which is preferably a Norland 3001 Processing Digital Oscilloscope manufactured by Norland Corporation.

Signal 33, which is representative of the rate of change of the engine cylinder pressure as has been previously described, is provided to the channel 4 data input of the computer 50. Signal 33 is utilized to derive the octane number of the test fuel as will be described more fully hereinafter.

The digital-to-analog converter outputs of the computer 50 are electrically connected to opposite poles of the potentiometer 61 (5KΩ). The wiper arm 62 of the potentiometer 61 is electrically connected to the non-inverting input of the operational amplifier 64 (Model 967 supplied by Analog Device Co.). The output signal 66 from the operational amplifier 64 is provided to the motor 67 which is associated with the pump setter 68 and is utilized to supply power to the motor 67. The drive shaft 69 of the motor 67 is utilized to set the pumping rate of the pump 25.

The potentiometer 71 is utilized to provide feedback information concerning the pumping rate of the pump 25. The wiper arm 73 of the potentiometer 71 moves in response to the position of the shaft 69 to indicate the pump flow rate. The wiper arm 73 is electrically connected through the parallel combination of resistors 74 (100KΩ) and 75 (10KΩ) and capacitor 77 (0.33 mf) to the inverting input of the operational amplifier 64.

A suitable pump setter 68 is a Motor Controlled Multi-turn Potentiometer No. 522-9505 distributed by Allied Electric. The manner in which the pump setter 68 and the circuitry associated with the pump setter 68 which interfaces the pump setter 68 to the computer 50 is utilized to manipulate the pumping rate of the pump 25 will be described more fully hereinafter.

A +5 volt power supply 81 supplies power to the RLY-2 relay 82 associated with the computer 50. When the relay 82 is closed, power is supplied from the +5 volt power supply 81 to the relay 84. When power is supplied from the +5 volt power supply 81, the relay 84 supplies power to the motor 85 which is associated with the valve driver 86. The shaft 88 associated with the motor 85 is utilized to manipulate the position of the selector valve 13.

A suitable valve driver 86 is a Hoke Operator part #0112,L2P manufactured by Hoke. The switches 89 associated with the valve driver 86 provide information regarding the position of the shaft 88 to the computer 50. The switches 89 are electrically connected to the DIN 4-DIN 7 inputs of the computer 50. The manner in which the valve driver 86 in conjunction with the computer 50 is utilized to control the position of the selector valve 13 will be described more fully hereinafter.

The +5 volt power supply 81 also supplies power for control by RLY-1 relay 91. When the relay 91 is closed, power is supplied from the +5 volt power supply 81 to the relay 92. When power is supplied from the +5 volt power supply 81, the relay 92 supplies power to the sample valve actuator 94. The sample valve actuator 94 provides an output signal 96 which may be pneumatic or electrical in form to the sample valve 50. Signal 96 is utilized to actuate sample valve 50 from its first position to its second position or from its second position to its first position. The sample valve actuator may be a normally closed Skinner solenoid valve manufactured by Skinner.

With the apparatus illustrated in FIG. 2 powered up and the computer programs set forth in Appendix I loaded into the computer 50, the digital-to-analog converter of the computer 50 establishes the pump flow rate required for the warm-up fuel to produce maximum knock from previously loaded density data. Preferably, the high octane reference fuel, low octane reference fuel and warm-up fuel are chosen to have the same density; thus, the same flow setting provides maximum knock for each of these fuels. Thus, it is necessary only to enter one density measurement for the warm-up fuel, high octane reference fuel and low octane reference fuel.

After the required flow rate has been entered into the computer 50, the engine 29 is then warmed up and the compression of the engine 29 is set based on the low octane reference fuel by the standard procedure set forth in ASTM 2699-79.

The output of the digital-to-analog converter of the computer 50 determines the voltage applied to the non-inverting input of the operational amplifier 64. The operational amplifier 64 compares the signal supplied by the Norland digital-to-analog converter through the potentiometer 61 to the voltage which is provided from the potentiometer 71 to the inverting input of the operational amplifier 64. The voltage applied to the inverting input of the operational amplifier 64 is proportional to the pumping rate of pump 25. The difference between the values of the signals applied to the inverting and non-inverting inputs of the operational amplifier 64 determines the magnitude of the signal which is provided from the output of the operational amplifier 64 to the motor 67. The pumping rate of the pump 25 is changed by the output of the operational amplifier 64 until the signals applied to the inverting and non-inverting inputs of the operational amplifier 64 are balanced. In this manner, the pumping rate of the pump 25 is controlled directly from the computer 50 by the digital-to-analog converter output of the computer 50.

After the engine 29 is warmed up, the computer 50 is supplied with the density of the test fuel, the octane number of the high octane reference fuel and the octane number of the low octane reference fuel. The computer is then allowed to run the high octane reference fuel, low octane reference fuel and test fuel through the engine 29. Data is acquired and the octane number of the test fuel is determined.

When it is desired during the program sequence to switch the selector valve 13, the Norland computer 50 closes the relay 82 which supplies 5 volts to the relay 84. The relay 84 is turned on and power is supplied to the motor 85. The motor 85 rotates the selector valve 13 so that various fuel ports are connected singularly to the suction inlet of the pump 25. A cam on the drive shaft 88 energizes the switches 89 which are connected to the binary input lines of the Norland computer 50. When the switch position to the desired fuel is reached, the computer 50 opens the relay 82 to stop the motor 85.

The computer 50 automatically changes the position of the selector valve 13 as required to provide the different fuels to the engine 29. The pumping rate of the pump 25 is automatically set and adjusted to the pumping rate that provides a flow rate of fuel to the engine 29 resulting in a maximum knock condition for each particular fuel.

When it is desired to supply the test fuel to the engine 29, the pumping rate of the pump 25 is automatically set and adjusted to the pumping rate that provides a flow rate of the test fuel to the engine 29 resulting in maximum knock conditions for the test fuel. The Norland computer 50 then closes the relay 91 which supplies 5 volts to the relay 92. The sample valve actuator 94 is then enabled to actuate the sample valve to the second position. This results in the test fuel contained in the sample loop of the sample valve being injected into the fuel flowing through conduit means 24 which may be the low octane reference fuel if the low octane reference fuel was the last fuel tested and there is a sufficient supply of the low octane reference fuel. After the test fuel has been injected into the fuel stream flowing to the engine 29, the sample valve 50 may be switched back to the first position by allowing the Norland Computer 50 open relay 91.

Data acquisition by the computer 50 consists of utilizing the shaft encoder 48 to trigger the computer 50. When the computer 50 is triggered, 1,024 data points 20 microseconds apart are acquired. This array of data is 20.48 milliseconds in length and centered about the combustion part of the engine cycle. This procedure is repeated 128 times and the results are acquired, similar data are acquired for the low octane reference fuel and the test fuel.

The thus acquired data is then processed to remove the low frequency normal combustion portion of the data and leave the higher frequency portion of the trace that is due to knocking combustion. The area of each of the traces that is due to knocking is then measured and stored in a register in the computer 50. The thus stored areas are directly related to the knock intensity and over a range of several octane numbers a plot of knock intensity versus octane number is a straight line. The reference fuel knock intensities are used to construct a calibration equation which is utilized to calculate the octane number of the test fuel.

Preferably, the data acquired by the computer 50 is Fourier transformed after averaging. This converts the data to the frequency domain and provides an easy means for filtering the low frequency terms. An inverse Fourier transform is then performed on the filtered data and the area of each trace is determined as has been previously described. Many other techniques could be utilized to process the data.

Figure 3:
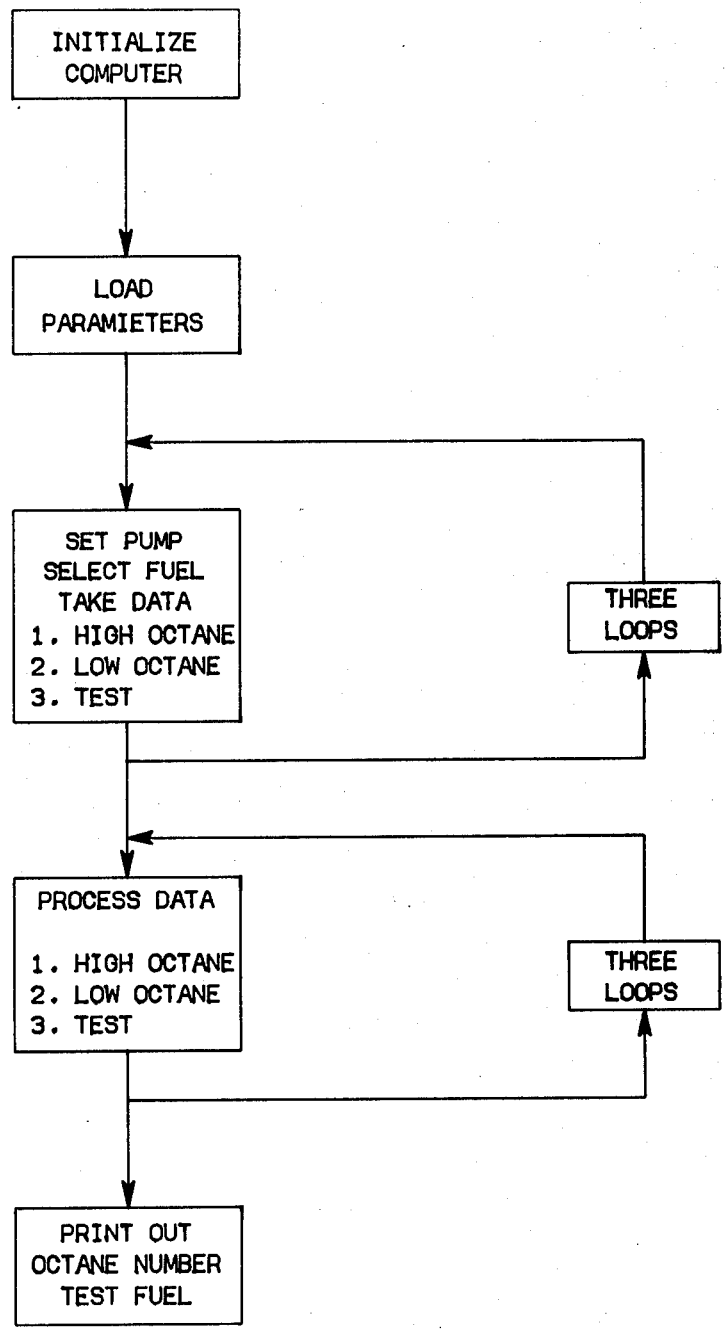
FIG. 3 is a flow chart illustrating the preferred method for determining the octane number of a fuel in accordance with the present invention.

A brief flow chart of the method of the present invention is illustrated in FIG. 3.

Many different types of software programs could be written in different languages and formats which would allow the Norland computer to carry out its required functions. While many different software programs could be developed to allow the Norland computer to accomplish its required functions, a suitable software program for the Norland computer is attached as Appendix I to the present application.

The invention has been described with particular reference to the standard ASTM methods for determining the octane number of gasoline. The ASTM methods require the use of the ASTM-CFR engine. It is again noted that the present invention is applicable to any octane measurement using any suitable engine.

The invention has been described broadly and in terms of the presently preferred embodiment. Reasonable variations and modifications are possible by those skilled in the art within the scope of the described invention and the appended claims.

That which is claimed is:

1. Apparatus comprising:
a sample valve means having at least first, second, third, fourth, fifth and sixth ports, said first and second ports being in fluid communication with each other, said third and fourth ports being in fluid communication with each other and said fifth and sixth ports being in fluid communication with each other when said sample valve means is in a first position and said first and sixth ports being in fluid communication with each other, said second and third ports being in fluid communication with each other and said fourth and fifth ports being in fluid communication with each other when said sample valve means is in a second position, said second and fifth ports being connected in fluid communication with each other through a sample loop;
means for supplying at least a first reference fuel having a first known octane number and a second reference fuel having a second known octane number different from said first known octane number to the third port of said sample valve means;
means for supplying a test fuel having an unknown octane number to the first port of said sample valve means;
an engine means having a fuel inlet;
means for supplying fuel from said fourth port to the fuel inlet of said engine means;
means for actuating said sample valve means to change the position of said sample valve means; and
means for establishing a first signal representative of the rate of change of the cylinder pressure in said engine means when said first reference fuel is flowing to said third port and said sample valve means is in said first position, for establishing a second signal representative of the rate of change of the cylinder pressure in said engine means when said second reference fuel is flowing to said third port and said sample valve means is in said first position, and for establishing a third signal representative of the rate of change of the cylinder pressure in said engine means when said sample valve means is actuated from said first position to said second position so as to supply said test fuel from said sample loop to said engine means.

2. Apparatus in accordance with claim 1 wherein said means for providing said first reference fuel and said second reference fuel to said third port comprises:

a pumping means having a suction inlet and a discharge outlet;

means for providing fuel from the discharge outlet of said pumping means to said third port;

means for providing said first reference fuel to the suction inlet of said pumping means; and means for manipulating the flow of said first reference fuel and said second reference fuel to the suction inlet of said pumping means in such a manner that only one fuel is provided to the suction inlet of said pumping means at any one time.

3. Apparatus in accordance with claim 2 additionally comprising means for manipulating the pumping rate of said pumping means in such a manner that said first reference fuel, said second reference fuel, and said test fuel are provided to the fuel inlet of said engine means at a desired flow rate.

4. Apparatus in accordance with claim 3 wherein said means for providing said first reference fuel to the suction inlet of said pumping means and said means for providing said second reference fuel to the suction inlet of said pumping means and said means for manipulating the flow of said first reference fuel and said second reference fuel to the suction inlet of said pumping means comprises:

a selector valve means having at least first and second input ports and at least one output port in fluid communication with the suction inlet of said pumping means;

a fuel reservoir for said first reference fuel having a fluid outlet in fluid communication with said first inlet port of said selector valve means;

a fuel reservoir for said second reference fuel having a fluid outlet in fluid communication with said second inlet port of said selector valve means; and means for manipulating said selector valve means so as to provide said first reference fuel and said second reference fuel sequentially to the suction inlet of said pumping means.

5. Apparatus in accordance with claim 1 wherein said means for establishing said first signal, said second signal and said third signal comprises a pressure transducer.

6. A method for determining the octane number of a test fuel comprising the steps of:

providing a first reference fuel, having a first known octane number, at a desired flow rate to the third port of a sample valve having at least first, second, third, fourth, fifth and sixth ports, said first and second ports being in fluid communication with each other, said third and fourth ports being in fluid communication with each other and said fifth and sixth ports being in fluid communication with each other when said sample valve is in a first position and said first and sixth ports being in fluid communication, said second and third ports being in fluid communication and said fourth and fifth ports being in fluid communication when said sample valve is in a second position, said second and fifth ports being connected in fluid communication with each other through a sample loop and said fourth port being connected in fluid communication with the fuel inlet of an engine;

establishing a first signal representative of the rate of change of the cylinder pressure in said engine when said first reference fuel is flowing to said third port and said sample valve is in said first position;

providing a second reference fuel, having a second known octane number different from said first known octane number, at a desired flow rate to said third port;

establishing a second signal representative of the rate of change of the cylinder pressure in said engine when said second reference fuel is flowing to said third port and said sample valve is in said first position;

providing a test fuel, having an unknown octane number, to said first port of said sample valve to thereby fill said sample loop with said test fuel;

actuating said sample valve to said second position after said sample loop is filled with said test fuel and while said second reference fuel is flowing to said third port at a desired flow rate for said test fuel to thereby inject the test fuel contained in said sample loop in said second reference fuel so as to provide the test fuel contained in said sample loop at a desired flow rate to said engine;

establishing a third signal representative of the rate of change of the cylinder pressure in said engine when said test fuel is flowing to the fuel inlet of said engine; and establishing the octane number of said test fuel in response to said first, second and third signals.

7. A method in accordance with claim 6 wherein said first reference fuel has an octane number of 94, said second reference fuel has an octane number of 90 and said test fuel has an octane number in the range of about 88 to about 95.

8. A method in accordance with claim 6 wherein said first reference fuel has an octane number of 100, said second reference fuel has an octane number of 96 and said test fuel has an octane number in the range of about 95 to about 100.

9. A method in accordance with claim 6 wherein said step of establishing the octane number of said test fuel in response to said first, second and third signals comprises:

acquiring a plurality of first arrays of data centered about the combustion part of the cycle of said engine when said first reference fuel is flowing to the fuel inlet of said engine;

averaging said first arrays of data;

filtering the low frequency normal combustion portion of the averaged first arrays of data;

determining a first knock intensity based on the filtered, averaged first arrays of data;

acquiring a plurality of second arrays of data when said second reference fuel is flowing to the fuel inlet of said engine;

averaging said second arrays of data;

filtering the low frequency normal combustion portion of the average second arrays of data;

determining a second knock intensity based on the filtered, averaged second arrays of data;

acquiring a plurality of third arrays of data when said test fuel is flowing to the fuel inlet of said engine;

averaging said third arrays of data;

filtering the low frequency normal combustion portion of the averaged third arrays of data;

determining a third knock intensity based on the filtered, averaged third arrays of data; and calculating the octane number of said test fuel based on a comparison of said first, second and third knock intensities.

* * * * *